(12) United States Patent
Meissner et al.

(10) Patent No.: US 6,362,384 B2
(45) Date of Patent: Mar. 26, 2002

(54) PREPARATION OF 1,2-DICHLOROETHANE

(75) Inventors: Ruprecht Meissner, Weisenheim; Michael Hesse, Worms; Christian Walsdorff, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/760,711

(22) Filed: Jan. 17, 2001

(30) Foreign Application Priority Data

Jan. 27, 2000 (DE) ......................................... 100 03 510

(51) Int. Cl.⁷ ............................................... C07C 17/00
(52) U.S. Cl. ...................................................... 570/203
(58) Field of Search ......................................... 570/203

(56) References Cited

U.S. PATENT DOCUMENTS

| 2,866,830 A | 12/1958 | Dunn |
| 3,184,515 A | 5/1965 | Penner |
| 4,046,821 A | * 9/1977 | Croce et al. ................. 570/203 |

FOREIGN PATENT DOCUMENTS

EP 0 206 265 12/1986

* cited by examiner

*Primary Examiner*—Alan Siegel
(74) *Attorney, Agent, or Firm*—Keil & Weinkauf

(57) ABSTRACT

A process for the preparation of 1,2-dichloroethane by oxychlorination of ethene in the presence of a copper-containing fixed-bed catalyst comprising a bed essentially consisting of catalyst particles which comprise, at least partially, support material impregnated with an active component and, if desired, a promoter, where the catalyst bed comprises essentially no separate inert material for dilution.

7 Claims, No Drawings

PREPARATION OF 1,2-DICHLOROETHANE

The invention relates to a process for the preparation of 1,2-dichloroethane by oxychlorination of ethene, to a catalyst employed in this process, and to a process for the preparation of the catalyst.

1,2-Dichloroethane is nowadays produced on an industrial scale by oxychlorination of ethene. In this process, ethene is reacted with hydrogen chloride and oxygen in the presence of a copper catalyst. Processes both in the gas phase on solid or fluidized catalysts and in the liquid phase using dissolved catalysts are available for the reaction, although only processes in the gas phase have been used on an industrial scale (see Ullmanns Enzyklopädie der technischen Chemie [Ullmann's Encyclopedia of Industrial Chemistry], $4^{th}$ Edition 1975, Volume 9, p. 428).

The present invention relates to an improvement to the fixed-bed process. In the fixed-bed process, the high exothermicity of the reaction causes problems which can, at relatively high space velocities as can occur in economical operation, result in the formation of so-called hot spots in the catalyst bed. The formation of such hot spots must be avoided under all circumstances since they are associated with deactivation of the catalyst by evaporation of the copper salt and damage to the catalyst moldings. For this reason, a catalyst bed with graduated activity profile is used in the fixed-bed processes of the prior art, with the activity of the catalyst bed increasing in the direction of flow. This is usually achieved by impregnating the catalyst with a graduated content of active components and, if desired, selective promoters. In addition to this, the catalyst bed is, in accordance with the prior art, diluted, at least in the reactor zones in which the driving force of the reaction is still very high, i.e. usually in the front region of the catalyst bed, with particles of an inert material, for example crushed graphite, tabletted or extruded graphite powder or non-impregnated catalyst support. Processes of this type are described in U.S. Pat Nos. 3,184,515 and 2,866,830.

However, the use of inert diluent materials such as graphite is accompanied by the significant disadvantage of an increased pressure loss, which has an effect, in particular, on use of low pressure-loss catalyst moldings and hinders material and heat transport in the axial direction. The conversion of pure graphite into low pressure-loss moldings is difficult and relatively expensive. The use of non-impregnated supports as diluent material is not recommended owing to the poor thermal conductivity, but in particular owing to the non-negligible activity of non-impregnated aluminum oxide supports for the formation of by-products. Excessive dilution of the active components on the support material is likewise unfavorable since this considerably impairs initiation of the reaction.

It is an object of the present invention to provide a process for the oxychlorination of ethene on a fixed-bed catalyst which manages without the presence of additional particles of an inert diluent material, even at high reactor space velocities.

We have found that this object is achieved by a process for the preparation of 1,2-dichloroethane by oxychlorination of ethene in the presence of a copper-containing fixed-bed catalyst comprising a bed essentially consisting of catalyst particles which comprise, at least partially, support material impregnated with an active component and, if desired, a promoter, where the catalyst bed comprises essentially no separate inert material for dilution.

A separate inert material is a chemically inert diluent material which is different from the catalyst particles and is not impregnated or cannot be impregnated. For the purposes of the present invention, inert material present in the catalyst particles is not a separate inert material. The term "essentially consisting of catalyst particles" means that the bed consists of at least 80% by weight, preferably at least 90% by weight, particularly preferably at least 95% by weight, and especially 100% by weight, of the catalyst particles.

The invention is based on the idea of arranging the individual catalyst particles of the catalyst bed so as to give a bed having a ratio between catalyst material and reactor volume which corresponds to the ratio of a catalyst bed diluted with particles of an inert material, so that dilution with additional particles of inert material is superfluous. This is achieved in that the individual catalyst particles have a filigree form or the individual catalyst particles contain inert diluent material in such proportions that the bed has said ratio of diluted beds known from the prior art.

The catalyst particles comprise, at least partially, support material impregnated with one or more active components and, if desired, one or more promoters. Suitable support materials which can be impregnated are known to the person skilled in the art and are described, for example, in Ullmanns Enzyklopädie der technischen Chemie [Ullmann's Encyclopedia of Industrial Chemistry], 4th Edition 1975, Volume 9, p. 429, and comprise aluminum oxides, silica gel and diatomaceous earth. Preferred support materials are aluminum oxides, for example $\gamma$-$Al_2O_3$. The catalyst support is preferably impregnated with a copper salt, for example with copper chloride, as active component and a conventional promoter, in the ratios known to the person skilled in the art, for example as described in Ullmanns Enzyklopädie der technischen Chemie [Ullmann's Encyclopedia of Industrial Chemistry], 4th Edition 1975, Volume 9, p. 429, and the literature cited therein. Preferred promoters are salts of the alkali, alkaline earth and rare-earth metals, particularly preferably salts of potassium, cesium and magnesium, such as potassium chloride or magnesium chloride. The catalyst support can, irrespective of the process used in the impregnation, be partially or preferably fully impregnated. The support is partially impregnated if it is merely impregnated at the surface.

The use of separate graphite particles for dilution of the catalyst bed can be avoided by means of one of the two following variants. These two variants can of course also be combined. Thus, firstly, it is possible to produce catalyst moldings comprising a mixture of a support material (for example aluminum oxide) and an inert material (for example graphite). After subsequent impregnation of the moldings, catalysts are obtained which, compared with moldings comprising exclusively the corresponding support material, with a comparable active component content (based on the proportion of support material) and a comparable space velocity over the catalyst bed, do not make further dilution with a separate inert material necessary. Such supports mixed with an inert material can be prepared in very low pressure-loss forms more simply than the pure inert material. In addition, the intimate mixing of support material and inert material produces a particularly homogeneous temperature profile. On the other hand, in a second variant, catalyst moldings can be selected which are distinguished by the fact that their bulk density is so low that the concentration of impregnated support material in the reactor, even without use of separate inert material, corresponds to the concentration of impregnated support material on use of conventional graphite-diluted catalyst beds.

The catalyst bed essentially consists of particles comprising the at least partially impregnated support material, where, in accordance with one embodiment of the invention, at least some of the catalyst particles have a geometry such that their bulk density before impregnation with the active component and, if desired, the promoters does not exceed 550 g/l.

The process according to the invention can, as described in Ullmanns Enzyklopädie der technischen Chemie [Ullmann's Encyclopedia of Industrial Chemistry], 4th Edition 1975, Volume 9, p. 429 ff., be carried out in tubular reactors containing the catalyst bed. The process can be carried out in one or a plurality of steps. The process can be carried out in a plurality of steps by adding the requisite oxygen in the form of pure oxygen or air in sub-streams divided over the plurality of reactors. The process can, if desired, be operated with circulated gas or in a simple mode. The reaction is generally carried out at a temperature of from 200 to 300° C. and a pressure of from 1 to 4 bar.

In one embodiment of the process according to the invention, the individual catalyst particles consist of the at least partially impregnated support material and have such a shape that a cavity volume of the resultant bed of from 45 to 80% by volume, preferably from 55 to 70% by volume, particularly preferably from 60 to 65% by volume, arises.

The catalyst particles preferably have one of the following shapes:

hollow cylinder;

cylinder with axial holes;

toothed wheel with one or more axial holes;

coaxial hollow cylinders with spokes which connect the outer hollow cylinder to the inner hollow cylinder (wagon wheel);

ring tablets;

domed ring tablets;

trilobes;

tetralobes.

A preferred shape of the catalyst particles is a cylinder having axial holes. The cylinder preferably has a diameter:height ratio of from 0.8:1 to 1.2:1, in particular 1:1, where the diameter and height of the cylinders preferably each vary from 4 to 8 mm. The cylinders preferably have up to 5, in particular from 2 to 4, axial holes.

The catalyst particles employed in accordance with the invention can, for example, have the shape of a cylinder having a hole (hollow cylinder), a diameter:height ratio of from 0.8:1 to 1.0:1 and a ratio of cylinder diameter:hole diameter of 1.5:1 (=diameter ratio). Catalyst particles of this type have a cavity volume of 60.8–68.7% by volume.

The catalyst particles can have, for example, two holes, a diameter:height ratio of from 0.8:1 to 1:1 and a diameter ratio of 2.3:1. Catalyst particles of this type have a cavity volume of 56.2–64.9% by volume.

The catalyst particles can, for example, have three holes, a diameter:height ratio of from 0.8:1 to 1:1 and a diameter ratio of 2.5:1. The cavity volume is then 63.3–70.7% by volume.

The catalyst particles can, for example, have four holes, a diameter:height ratio of from 0.8:1 to 1:1 and a diameter ratio of 3.0:1. The cavity volume is then 60.8–68.7% by volume.

A further example is a cylinder having the dimensions 7×7 mm and four equidistant axial holes having a diameter of 1.75 mm.

The catalyst particles employed in accordance with the invention can have, for example, the shape of a trilobe shown in FIG. 1. The d2/a ratio here is preferably from 1.0:1 to 1.4:1 and the d2/d1 ratio is preferably 1.4–1.8:1. A trilobe having d2/a=1.2:1 and d2/d1=1.6:1 has a cavity volume of 62.7% by volume.

The catalyst particles employed in accordance with the invention can have, for example, the shape of a tetralobe shown in FIG. 2. D can be, for example, from 4 to 10 mm, d1 from 1.2 to 3.0 mm and d2=D/2, where, at a diameter D:height ratio of 1:1, the cavity volume is 67.7% by volume. With diameter D=height, d2=D/2 and d1=D/2 −D/K, the cavity volume for K=2, 3, 4, 5 and 10 is 42.3% by volume, 50.1% by volume, 60.1% by volume, 67.7% by volume and 87.4% by volume respectively.

A further preferred shape of the catalyst particles is a toothed wheel, preferably having a central hole. The toothed wheel is preferably regular, i.e. it is circumscribed by a circle, with the tips of the teeth touching the circle line. The ratio of circle diameter of the circumscribing circle D to the diameter of the inner circle of the teeth $D_i$ is preferably from 1.2:1 to 1.8:1, with the ratio of circle diameter D to diameter of the hole $d_i$ in each case preferably varying from 1.8:1 to 2.4:1. The toothed wheel preferably has from 5 to 10 teeth, in particular 7 teeth.

An example is a toothed wheel having 7 teeth with $D/D_i=1.6$ and $D/d_i=2.2$, with a cavity volume of 65.6% by volume.

A further preferred shape of the catalyst particles is that of a wagon wheel.

An example is a wagon wheel having a diameter of the outer ring of 25 mm and a diameter of the inner ring of 9 mm, with 6 spokes, where the wall thickness of the spokes is in each case 1.0 mm and that of the rings (hollow cylinders) is in each case 1.5 mm. A wagon wheel of this type has a cavity volume of 62.3% by volume.

A further example is a wagon wheel having an outer ring with a diameter of 8 mm, an inner ring with a diameter of 1.6 mm, 5 spokes with a wall thickness of 0.6 mm and a wall thickness of the rings of 0.8 mm. Wagon wheels of this type have, as bulk material, a cavity volume of 61.7% by volume.

In a further embodiment of the process according to the invention, the bed comprises catalyst particles which comprise a chemically inert diluent material which cannot be impregnated. The catalyst bed preferably consists of catalyst particles of this type.

The catalyst particles comprising the inert diluent material generally comprise from 5 to 80% by weight, preferably from 5 to 60% by weight, particularly preferably from 10 to 40% by weight, of the inert diluent material. Preferred inert diluent materials are finely divided graphite, ground quartz or cordierite, for example in the form of graphite powder, quartz sand or cordierite.

The present invention also relates to the catalyst particles comprising the inert diluent material themselves.

The catalyst particles comprising the inert diluent material can have any conventional shape. In principle, low pressure-loss moldings are preferred. Examples are spheres, bars, tablets and rings. They can likewise have the above-defined shapes of a hollow cylinder, a cylinder having a plurality of axial holes, a toothed wheel, a wagon wheel, a trilobe or a tetralobe.

The catalyst particles comprising the inert diluent material can be produced in a process comprising the following steps:

i) mixing of support material which can be impregnated, inert diluent material and, if desired, conventional extrusion and tabletting assistants;

ii) tabletting or extrusion of the resultant mixture;

iii) drying and calcination of the resultant tablets or extrudates;

iv) impregnation of the tablets or extrudates with the active component and, if desired, the promoters.

Support material, inert diluent material and, if desired, conventional tabletting assistants are mixed in a manner known to the person skilled in the art and tabletted or extruded to give catalyst particles. The calcination is carried out at temperatures of, preferably, from 400 to 800° C. The calcined catalyst particles obtained in this way are subsequently impregnated with an aqueous or alcoholic solution containing a copper chloride and the promoter by conventional methods, for example by soaking or spraying. This may be followed by a drying step. The impregnation can be carried out by spraying the solution onto the heated catalyst support, during which the solvent evaporates before the solution is able to penetrate into the catalyst particles. An only superficial, i.e. partial impregnation of the support material can thereby be achieved. The support material can also be impregnated fully.

By omitting the dilution of the catalyst bed with additional particles of inert material, a very low pressure loss arises in the reactor. The increased material and heat transport caused by this and the resultant homogeneous temperature profile allow either higher space velocities and thus better space-time yields or, for constant space velocity, higher selectivities.

We claim:

1. A process for the preparation of 1,2-dichloroethane by oxychlorination of ethene in the presence of a copper-containing fixed-bed catalyst comprising a bed essentially consisting of catalyst particles which comprise, at least partially, support material impregnated with an active component and, optionally, a promoter, where the catalyst bed comprises essentially no separate inert material for dilution, and wherein at least some of the catalyst particles have a shape such that their bulk density before impregnation with the active component and, optionally, the promoters does not exceed 550 g/l.

2. A process as in claim 1, wherein the bed comprises catalyst particles whose shape is selected from the following:

hollow cylinder;

cylinder with axial holes;

toothed wheel with one or more axial holes;

coaxial hollow cylinders with spokes which connect the outer hollow cylinder to the inner hollow cylinder (wagon wheel);

ring tablets;

domed ring tablets;

trilobes;

tetralobes.

3. A process as claimed in claim 1, wherein the bed comprises catalyst particles which additionally comprise a chemically inert diluent material which cannot be impregnated.

4. A process as claimed in claim 3, wherein the inert diluent material is graphite, finely divided quartz, steatite or cordierite.

5. A process as claimed in claim 1, wherein the active component is a copper salt.

6. A process as claimed in claim 1, wherein the support material which can be impregnated is an aluminum oxide.

7. A process as claimed in claim 1, wherein the promoter is a potassium, cesium or magnesium salt.

* * * * *